United States Patent
Kapadia

(10) Patent No.: US 12,390,288 B2
(45) Date of Patent: Aug. 19, 2025

(54) STERILE INTERFACE MODULE FOR ROBOTIC SURGICAL ASSEMBLIES

(71) Applicant: Covidien LP, Mansfield, MA (US)

(72) Inventor: Jaimeen Kapadia, Cambridge, MA (US)

(73) Assignee: Covidien LP, Mansfield, MA (US)

(*) Notice: Subject to any disclaimer, the term of this patent is extended or adjusted under 35 U.S.C. 154(b) by 681 days.

(21) Appl. No.: 17/631,705

(22) PCT Filed: Aug. 25, 2020

(86) PCT No.: PCT/US2020/047770
§ 371 (c)(1),
(2) Date: Jan. 31, 2022

(87) PCT Pub. No.: WO2021/041395
PCT Pub. Date: Mar. 4, 2021

(65) Prior Publication Data
US 2022/0265374 A1    Aug. 25, 2022

Related U.S. Application Data

(60) Provisional application No. 62/892,620, filed on Aug. 28, 2019.

(51) Int. Cl.
*A61B 34/30* (2016.01)
*B25J 9/00* (2006.01)

(52) U.S. Cl.
CPC ............. *A61B 34/30* (2016.02); *B25J 9/0009* (2013.01)

(58) Field of Classification Search
CPC ... A61B 34/30; A61B 34/74; A61B 2034/302; A61B 34/37; A61B 2017/00477;
(Continued)

(56) References Cited

U.S. PATENT DOCUMENTS 9,033,958 B2 * 5/2015 Mailloux ............... A61B 34/30
606/1
9,271,705 B2 * 3/2016 Vaughn ................... B23B 31/22
(Continued)

FOREIGN PATENT DOCUMENTS

CN    105163685 A    12/2015
CN    107666877 A    2/2018
(Continued)

OTHER PUBLICATIONS

European Search Report Dated Jul. 26, 2023 for European Patent Application No. 20855949.2 (16 pages).
(Continued)

*Primary Examiner* — Jennifer Pitrak McDonald
*Assistant Examiner* — Michael T. Holtzclaw
(74) *Attorney, Agent, or Firm* — Carter, DeLuca & Farrell LLP

(57) ABSTRACT

A robotic surgical assembly includes an instrument drive unit and a sterile interface module for coupling an electromechanical robotic surgical instrument to the instrument drive unit. The sterile interface module is detachable from the instrument drive unit and is equipped with a mechanism that allows for a manual actuation of the surgical instrument.

25 Claims, 10 Drawing Sheets

(58) Field of Classification Search
CPC .......... A61B 2017/00398; B25J 9/0009; B25J 15/0066; B25J 15/04
USPC ...................................................... 606/1, 130
See application file for complete search history.

(56) References Cited

U.S. PATENT DOCUMENTS

| | | | |
|---|---|---|---|
| 11,890,070 B2* | 2/2024 | Lambrecht | ............ A61B 34/30 |
| 2013/0245647 A1 | 9/2013 | Martin et al. | |
| 2016/0081754 A1 | 3/2016 | Kostrzewski et al. | |
| 2016/0151115 A1* | 6/2016 | Karguth | ............ A61B 1/00149 606/41 |
| 2017/0135773 A1 | 5/2017 | Lohmeier et al. | |
| 2018/0126546 A1* | 5/2018 | Vaders | ................. B25J 9/0009 |
| 2018/0168752 A1 | 6/2018 | Scheib et al. | |
| 2019/0021801 A1* | 1/2019 | Radgowski | ............ A61B 34/30 |
| 2019/0254763 A1* | 8/2019 | Lambrecht | ............ A61B 34/30 |
| 2020/0060516 A1* | 2/2020 | Baez, Jr. | ............ A61B 1/0053 |
| 2020/0222130 A1* | 7/2020 | Cooper | ................. A61B 34/70 |
| 2021/0093403 A1* | 4/2021 | Betsugi | ................. A61B 34/30 |

FOREIGN PATENT DOCUMENTS

| | | |
|---|---|---|
| CN | 109219414 A | 1/2019 |
| EP | 3616641 A1 | 3/2020 |
| WO | 2017205308 A1 | 11/2017 |
| WO | 2017205329 A1 | 11/2017 |

OTHER PUBLICATIONS

International Search Report dated Nov. 30, 2020, issued in corresponding international application No. PCT/US2020/047770, 4 pages.
Suplementary European Search Report Dated Oct. 30, 2023 for European Patent Application No. 20855949.2 (15 pages).
Chinese Office Action issued in corresponding Chinese Application No. 202080054453.6 dated Apr. 10, 2025, 15 pages.

* cited by examiner

STERILE INTERFACE MODULE FOR ROBOTIC SURGICAL ASSEMBLIES

TECHNICAL FIELD

The disclosure relates to robotics, and more specifically to robotic surgical devices, assemblies, and/or systems for performing endoscopic surgical procedures and methods of use thereof.

BACKGROUND

Robotic surgical systems have been used in minimally invasive medical procedures. Some robotic surgical systems include a console supporting a surgical robotic arm and a surgical instrument mounted to the robotic arm. The surgical instrument may have an elongated shaft that supports at least one end effector (e.g., forceps or a grasping tool) on a distal end thereof. In some robotic surgical systems, the entire length of the elongated shaft of the surgical instrument must pass through a holder or other feature of the robotic arm, thereby making removal or exchange of the surgical instrument from the robotic arm cumbersome.

Manually-operated surgical instruments often include a handle assembly for actuating the functions of the surgical instrument; however, when using a robotic surgical system, no handle assembly is typically present to actuate the functions of the end effector. It is the robotic arm of the robotic surgical system that provides mechanical power to the surgical instrument for its operation and movement. Each robotic arm may include an instrument drive unit that is operatively connected to the surgical instrument by an interface. The interface couples the selected surgical instrument to the robotic surgical system for driving operations of the surgical instrument and to provide structure for ready removal or exchange of the surgical instrument from the robotic arm.

During a surgical procedure, some portions of the surgical instrument may be exposed to a non-sterile environment or non-sterile components. Such exposure may contaminate the surgical instrument, or portions thereof. Since it is imperative that many of the components of the robotic surgical system remain sterile, there is a need to maintain sterility at the interface used to couple the surgical instrument to the robotic surgical system for protecting sterile components of the robotic surgical system from being contaminated by the non-sterile portions of the surgical instrument. A need also exists for a robotic surgical system that enables more efficient and expeditious removal or exchange of a surgical instrument and which has improved usability.

SUMMARY

In accordance with an aspect of the disclosure, an interface module is provided for coupling an electromechanical robotic surgical instrument to an instrument drive unit. The interface module includes a collar configured to be coupled to the instrument drive unit, a button movably coupled to the collar, and a drive transfer assembly. The drive transfer assembly includes a distal end portion and a proximal end portion movably coupled to the distal end portion. The distal end portion is configured to couple to a driven member of the electromechanical robotic surgical instrument, and the proximal end portion is configured to selectively couple to a drive member of the instrument drive unit. The proximal end portion of the drive transfer assembly is configured to move distally, in response to an actuation of the button, to disengage from the drive member of the instrument drive unit.

In aspects, the button may be movable along a first axis to move the proximal end portion of the drive transfer assembly along a second axis, perpendicular to the first axis, between an engaged position and a disengaged position. In the engaged position, the drive transfer assembly is engaged with the drive member of the instrument drive unit. In the disengaged position, the drive transfer assembly is disengaged from the drive member of the instrument drive unit.

In some aspects, the interface module may further include a slider supported on the proximal end portion of the drive transfer assembly and configured to engage the button. The proximal end portion of the drive transfer assembly may be configured to move axially with the slider.

In further aspects, the slider may have a camming surface and the button may have a camming surface configured to engage the camming surface of the slider to distally move the slider, and in turn, the proximal end portion of the drive transfer assembly.

In other aspects, the interface module may further include a hub. The hub may house the slider and the proximal end portion of the drive transfer assembly.

In aspects, the instrument drive unit may further include a pull tab movably coupled to the collar and configured to releasably couple the interface module to the instrument drive unit.

In some aspects, the interface module may further include a hub defining an aperture therein. The pull tab may include a protrusion configured to be received in the aperture of the hub to axially fix the hub to the collar.

In further aspects, the pull tab may be manually movable between a first position and a second position. In the first position, the protrusion of the pull tab is engaged with the aperture of the hub whereby the hub is lockingly engaged with the collar. In the second position, the protrusion of the pull tab is disengaged from the aperture of the hub whereby the hub is unlocked from the collar.

In another aspect, the pull tab may be configured to lockingly engage the button when the button is actuated, such that the pull tab maintains the button in an actuated position to maintain the proximal end portion of the drive transfer assembly disengaged from the drive member of the instrument drive unit.

In other aspects, the pull tab may have a latch and the button may have a latch that engages the latch of the pull tab when the button is moved to the actuated position. The latch of the pull tab may be configured to resist movement of the button out of the actuated position.

In aspects, the pull tab may be configured to move between an inward position and an outward position. The latch of the pull tab may be configured to disengage the latch of the button in response to movement of the pull tab toward the outward position.

In some aspects, the interface module may further include a gear selectively engagable with the distal end portion of the drive transfer assembly and manually rotatable to rotate the distal end portion of the drive transfer assembly when the drive transfer assembly is disengaged from the drive member of the instrument drive unit.

In further aspects, the distal end portion of the drive transfer assembly may have gear teeth extending thereabout.

In other aspects, the gear may be slidable relative to the drive transfer assembly between a first position, in which the gear is disengaged from the gear teeth of the distal end portion of the drive transfer assembly, and a second position, in which the gear is engaged with the gear teeth of the distal end portion of the drive transfer assembly.

In another aspect of the disclosure, a sterile interface module for coupling an instrument drive unit and a surgical instrument is provided. The sterile interface module includes a body member configured to selectively couple to a surgical instrument, a hub supported on the body member, a plurality of drive transfer assemblies supported on the body member, and a slider. Each of the drive transfer assemblies includes a proximal end portion configured to selectively couple to a drive member of an instrument drive unit, and a distal end portion configured to selectively couple to a driven member of the surgical instrument. The proximal end portion is axially movable relative to the distal end portion. The slider is supported on the proximal end portion of each of the drive transfer assemblies. The proximal end portion of the drive transfer assemblies is configured to move distally relative to the respective distal end portion of the drive transfer assemblies to disengage from the respective drive member of the instrument drive unit in response to distal movement of the slider.

In aspects, the slider may define a plurality of openings therethrough. The proximal end portions of the drive transfer assemblies may extend through the respective openings.

In some aspects, the slider may include an end portion having a camming surface.

In further aspects, the sterile interface module may further include a gear rotationally supported on the body member and configured to selectively engage the distal end portion of one of the drive transfer assemblies.

In another aspect, the gear may be slidable relative to the body member between a first position, in which the gear is disengaged from the distal end portion of the drive transfer assembly, and a second position, in which the gear is engaged to the distal end portion of the drive transfer assembly.

In other aspects, hub may have a squared configuration and may include a first side and a second side adjoining the first side. The first side may define a pair of apertures for receipt of a pair of protrusions of a pull tab. The second side may define a passage for receipt of a button.

In accordance with yet another aspect of the disclosure, a sterile interface module is provided and includes a pull tab having a protrusion, a drive transfer assembly, and a hub. The drive transfer assembly is for coupling a driven member of an electromechanical robotic surgical instrument and a drive member of an instrument drive unit. The hub has a portion of the drive transfer assembly disposed therein. The hub defines an aperture configured for receipt of the protrusion of the pull tab. The pull tab is configured to move between a first position and a second position. In the first position, the protrusion of the pull tab is engaged with the aperture of the hub to axially fix the interface module to the instrument drive unit. In the second position, the protrusion of the pull tab is disengaged from the aperture of the hub.

In aspects, the pull tab may be resiliently biased toward the first position.

In some aspects, the sterile interface module may further include a button operably coupled to the drive transfer assembly and configured to disconnect the drive transfer assembly from the drive member of the instrument drive unit when the button is in an actuated position.

In further aspects, the pull tab may be configured to lockingly engage the button, such that the pull tab maintains the button in the actuated position to maintain the drive transfer assembly disconnected from the drive member of the instrument drive unit.

In other aspects, the pull tab may have a latch and the button may have a latch that engages the latch of the pull tab when the button is moved to the actuated position. The latch of the pull tab may be configured to resist movement of the button out of the actuated position.

In another aspect, the pull tab may be configured to move between an inward position and an outward position. The latch of the pull tab may be configured to disengage the latch of the button in response to movement of the pull tab toward the outward position.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein.

DETAILED DESCRIPTION

Figure 1:
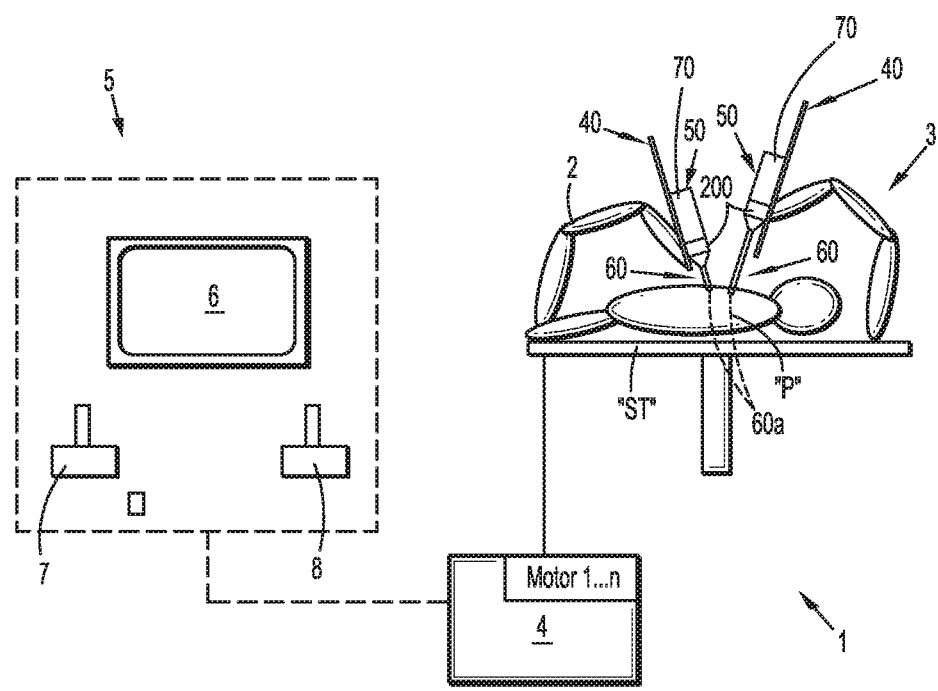
FIG. 1 is a schematic illustration of a robotic surgical system including an instrument drive unit, a sterile interface module, and a surgical instrument.
Figure 2:
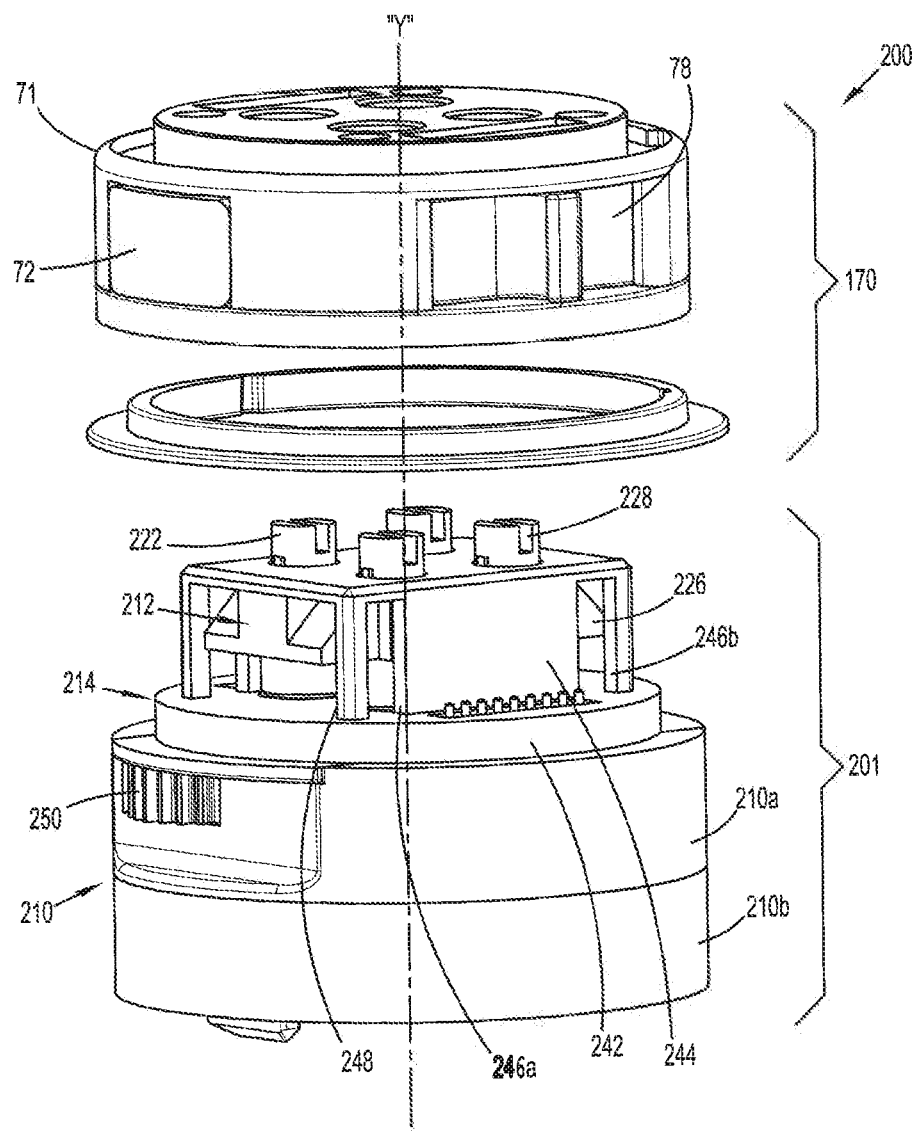
FIG. 2 is a perspective view, with parts separated, of the sterile interface module of FIG. 1.

Embodiments of the disclosure are described in detail with reference to the drawings, in which like reference numerals designate identical or corresponding elements in each of the several views. As used herein, the term "distal" refers to that portion of the robotic surgical system or component thereof that is closer to a patient, while the term "proximal" refers to that portion of the robotic surgical system or component thereof that is farther from the patient.

As used herein, the terms parallel and perpendicular are understood to include relative configurations that are substantially parallel and substantially perpendicular up to about + or −10 degrees from true parallel and true perpendicular.

As used herein, the term "clinician" refers to a doctor, nurse, or other care provider and may include support personnel. In the following description, well-known functions or construction are not described in detail to avoid obscuring the disclosure in unnecessary detail.

Throughout the disclosure, components of the robotic surgical system described herein may have two or more duplicates thereof. In the interest of brevity, only one of the duplicate components will be described in detail. It can be assumed that the duplicate components not described in detail have identical features and/or functions or substantially identical features and/or functions as its sister component.

Referring initially to FIG. 1, a surgical system, such as, for example, a robotic surgical system 1, generally includes one or more surgical robotic arms 2, 3, a control device 4, and an operating console 5 coupled with control device 4. Any of the surgical robotic arms 2, 3 may have a robotic surgical assembly 50 and an electromechanical surgical instrument 60 coupled thereto. The robotic surgical assembly 50 further includes an instrument drive unit 70 and a coupling assembly or sterile interface module 200 that couples the electromechanical surgical instrument 60 to the instrument drive unit 70 as described in greater detail below. In some embodiments, the robotic surgical assembly 50 may be removably attached to a slide rail 40 of one of the surgical robotic arms 2, 3. In certain embodiments, the robotic surgical assembly 50 may be fixedly attached to the slide rail 40 of one of the surgical robotic arms 2, 3.

Operating console 5 includes a display device 6, which is set up to display three-dimensional images; and manual input devices 7, 8, by means of which a clinician (not shown), is able to telemanipulate the robotic arms 2, 3 in a first operating mode, as known in principle to a person skilled in the art. Each of the robotic arms 2, 3 may be composed of any number of members, which may be connected through joints. The robotic arms 2, 3 may be driven by electric drives (not shown) that are connected to control device 4. The control device 4 (e.g., a computer) is set up to activate the drives, for example, by means of a computer program, in such a way that the robotic arms 2, 3, the attached robotic surgical assembly 50, and thus the electromechanical surgical instrument 60 (including an electromechanical end effector 60a thereof) execute a desired movement according to a movement defined by means of the manual input devices 7, 8. The control device 4 may also be set up in such a way that it regulates the movement of the robotic arms 2, 3 and/or of the drives.

The robotic surgical system 1 is configured for use on a patient "P" positioned (e.g., lying) on a surgical table "ST" to be treated in a minimally invasive manner by means of a surgical instrument such as the electromechanical surgical instrument 60. The robotic surgical system 1 may also include more than two robotic arms 2, 3, the additional robotic arms likewise connected to the control device 4 and telemanipulatable by means of the operating console 5. A surgical instrument, for example, the electromechanical surgical instrument 60, may also be attached to any additional robotic arm(s).

Figure 3:
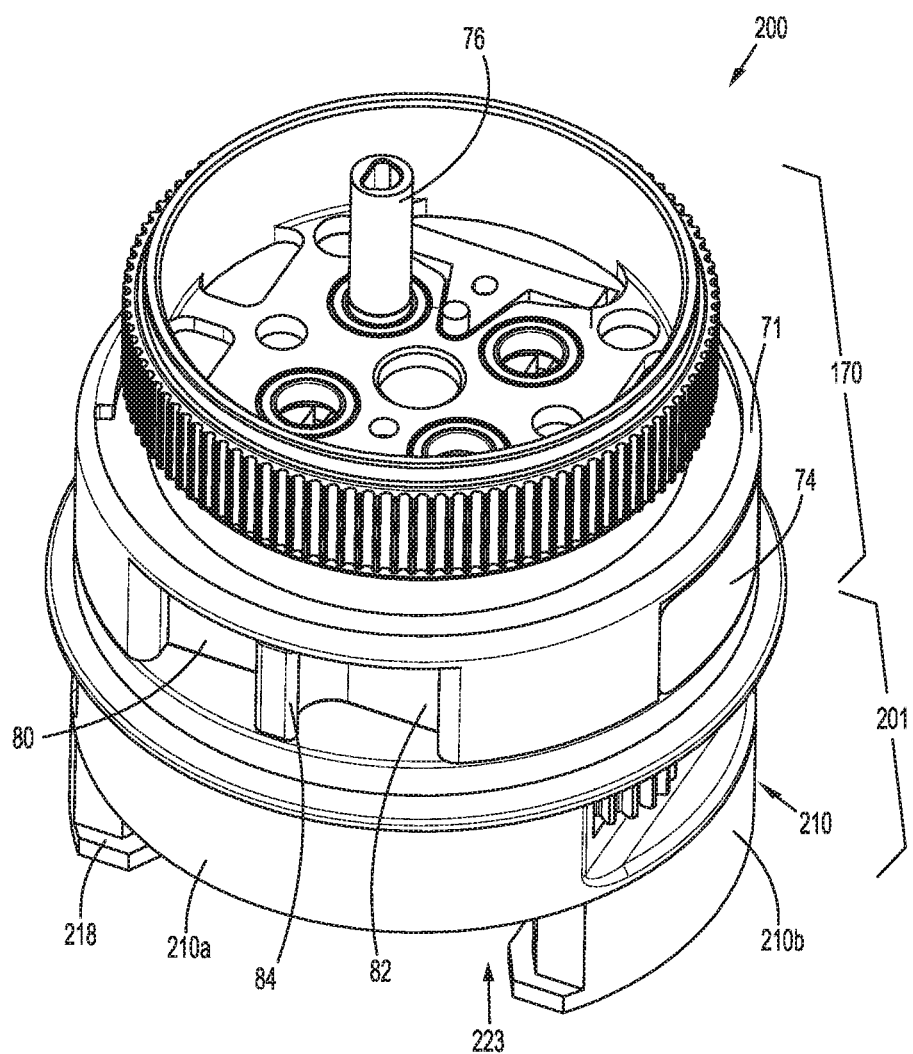
FIG. 3 is a top, perspective view of the sterile interface module connected to a drive member of the instrument drive unit of FIG. 1.

The control device 4 may control one or more motors, e.g., motors (Motor 1 . . . n), each motor configured to drive movement of the robotic arms 2, 3 in any number of directions. Further, the control device 4 may control the instrument drive unit 70 including a motor assembly (not explicitly shown) thereof that drives various operations of the end effector 60a of the electromechanical surgical instrument 60. The motor assembly of the robotic surgical assembly 50 includes any number of motors that couple to the sterile interface module 200 via a corresponding number of drive members 76 (FIG. 3) extending from the motors.

In general, the robotic surgical assembly 50 transfers power and actuation forces (e.g., torque) from the motors of the motor assembly of the instrument drive unit 70, through the sterile interface module 200, to driven members (not explicitly shown) supported within an instrument housing (not explicitly shown) of the electromechanical surgical instrument 60. Such transfer of power and actuation forces ultimately drives movement of components of the end effector 60a of the electromechanical surgical instrument 60 for operating the electromechanical surgical instrument 60. This movement may include, for example, a movement of a knife blade (not shown) and/or a closing and opening of jaw members (not shown) of the end effector 60a, an articulation/rotation/pitch/yaw of the end effector 60a, and/or the actuation or firing of the end effector 60a (e.g. a stapling portion of the end effector 60a).

With reference to FIGS. 2-6B, the sterile interface module 200 of the robotic surgical assembly 50 is provided for selectively interconnecting the robotic surgical assembly 50 and the electromechanical surgical instrument 60. The electromechanical surgical instrument 60 may be laterally coupled (e.g., side-loaded) to, or laterally decoupled from, the sterile interface module 200 of the robotic surgical assembly 200. In general, the sterile interface module 200 functions to provide an interface between the instrument drive unit 70 and an electromechanical surgical instrument such as electromechanical surgical instrument 60. This interface advantageously maintains sterility, provides a means to transmit electrical communication between the robotic surgical assembly 50 and the electromechanical surgical instrument 60, provides structure configured to transfer rotational force from the robotic surgical assembly 50 to the electromechanical surgical instrument 60 for performing a function with the electromechanical surgical instrument 60, and/or provides structure to selectively attach/remove the electromechanical surgical instrument 60 to/from the robotic surgical assembly 50 (e.g., for rapid instrument exchange). In aspects, the interface module 200 may become sterile via a sterilization process performed before or after a procedure and/or be sterilized during manufacturing.

The sterile interface module 200 includes a release assembly 170 coupled to the instrument drive unit 70, and a main assembly 201 coupled between the release assembly 170 and the surgical instrument 60. The release assembly 170 is configured to selectively release or detach the main assembly 201 of the sterile interface module 200 from the instrument drive unit 70 and includes a collar or body portion 71, and a pair of buttons 72, 74 and a pair of tabs, such as, for example, pull tabs 78, 80, each of which being supported in corresponding slots in the collar 71. The buttons 72, 74 face opposite one another and are disposed on opposite sides of the collar 71, and the pull tabs 78, 80 face opposite one another and are disposed on opposite sides of the collar 71, such that the buttons 72, 74 and pull tabs 78, 80 are all oriented to face a central longitudinal axis "Y" defined by the sterile interface module 200.

The pull tabs 78, 80, which are spring biased by one or more springs 83 (FIG. 6A) toward an inward position, may be simultaneously pulled to an outward position (FIG. 6B) to release the main assembly 201 of the sterile interface module 200 from the release assembly 170 of the sterile interface module 200, and therefore from the instrument drive unit 70. In some aspects, the release assembly 170 may only include one pull tab. Each of the pull tabs 78, 80 may have a generally U-shaped configuration and includes a body portion 82, a stem 84 extending outwardly from the body portion 82, and a pair of protuberances or protrusions 86, 88 extending inwardly from the body portion 82. The stems 84 of the pull tabs 78, 80 are configured to be grasped by a clinician, and the protrusions 86, 88 are configured to selectively engage with one or more attachment apertures 246a, 246b (described in greater detail below) of the sterile interface module 200 to selectively secure the sterile interface module 200 to the instrument drive unit 70. The protrusions 86, 88 each have a ramped surface 90, 93 and a latch feature 92, such as, for example, a hook, configured to engage with corresponding ramped surfaces 120, 122 (FIG. 5) and latch features 126 of the buttons 72, 74. In aspects, the ramped surfaces 90, 93 may be formed on the latch feature 92.

Figure 6A:
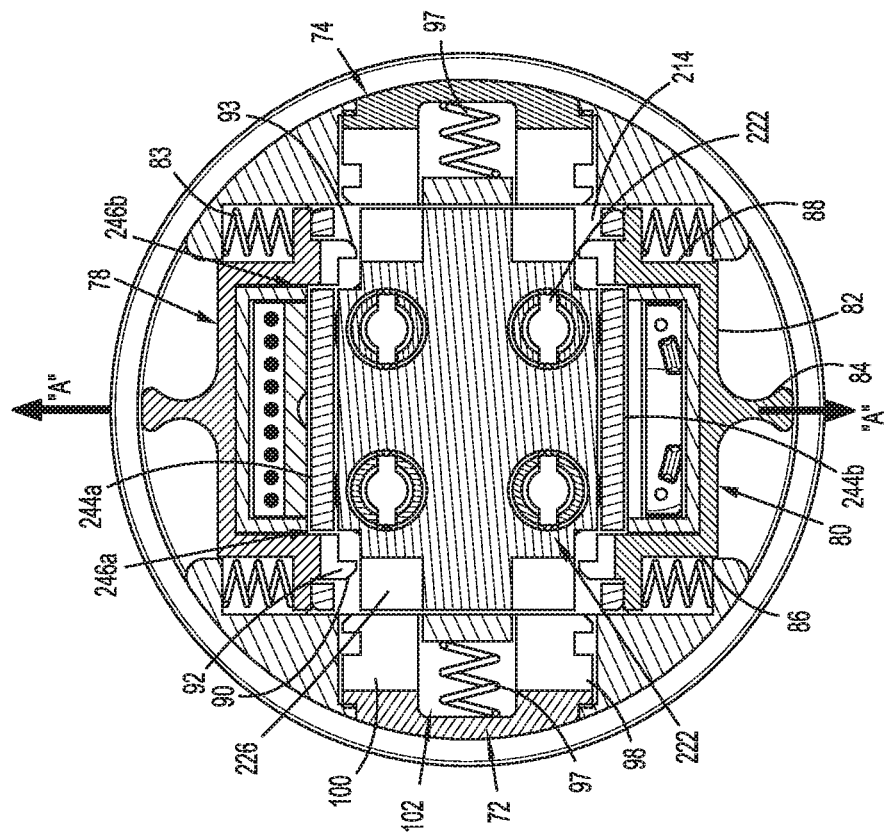
FIG. 6A is a transverse cross-sectional view illustrating the pull tabs engaged with a hub of the sterile interface module, and the buttons disengaged from the hub.
Figure 6B:
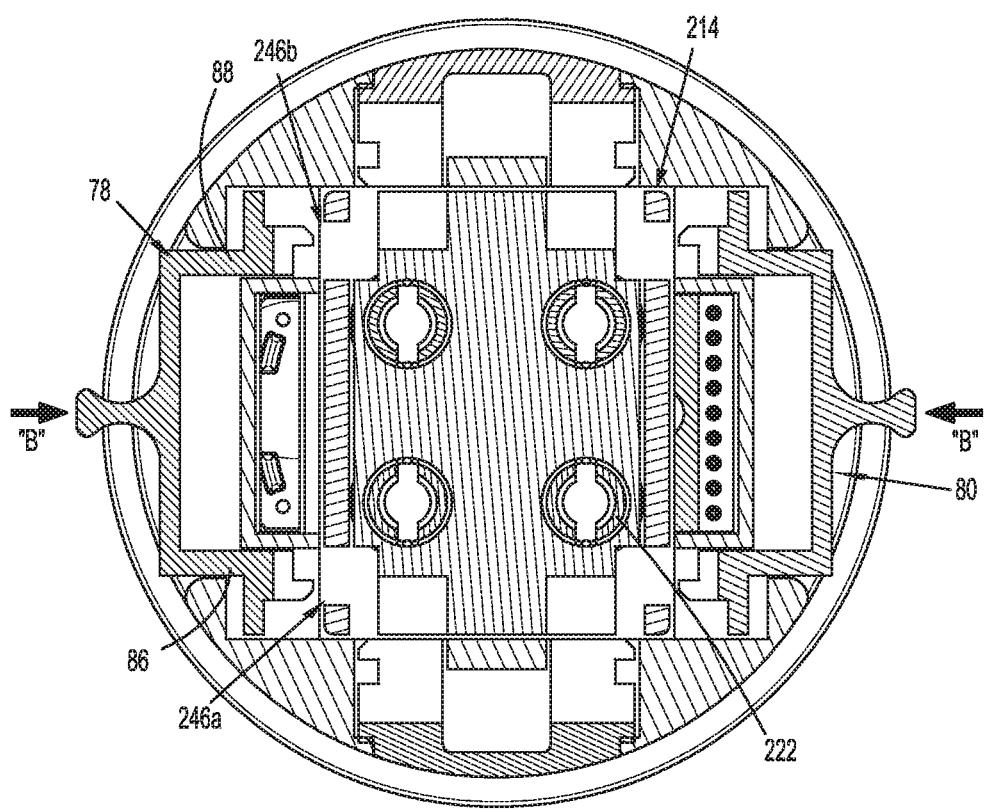
FIG. 6B is a transverse cross-sectional view illustrating the pull tabs disengaged from the hub.

With the sterile interface module 200 attached to the instrument drive unit 70, pulling of the pull tabs 78, 80 outwardly moves the protrusions 86, 88 of the respective pull tabs 78, 80 relative to the attachment apertures 246a, 246b of the sterile interface module 200, as seen in FIG. 6B. Such relative movement separates the pull tabs 78, 80 of the release assembly 170 from a hub 214 of the main assembly 201, whereby the main assembly 201 can separate from the instrument drive unit 70 (e.g., by pulling the sterile interface module 200 away from the instrument drive unit 70).

Figure 5:
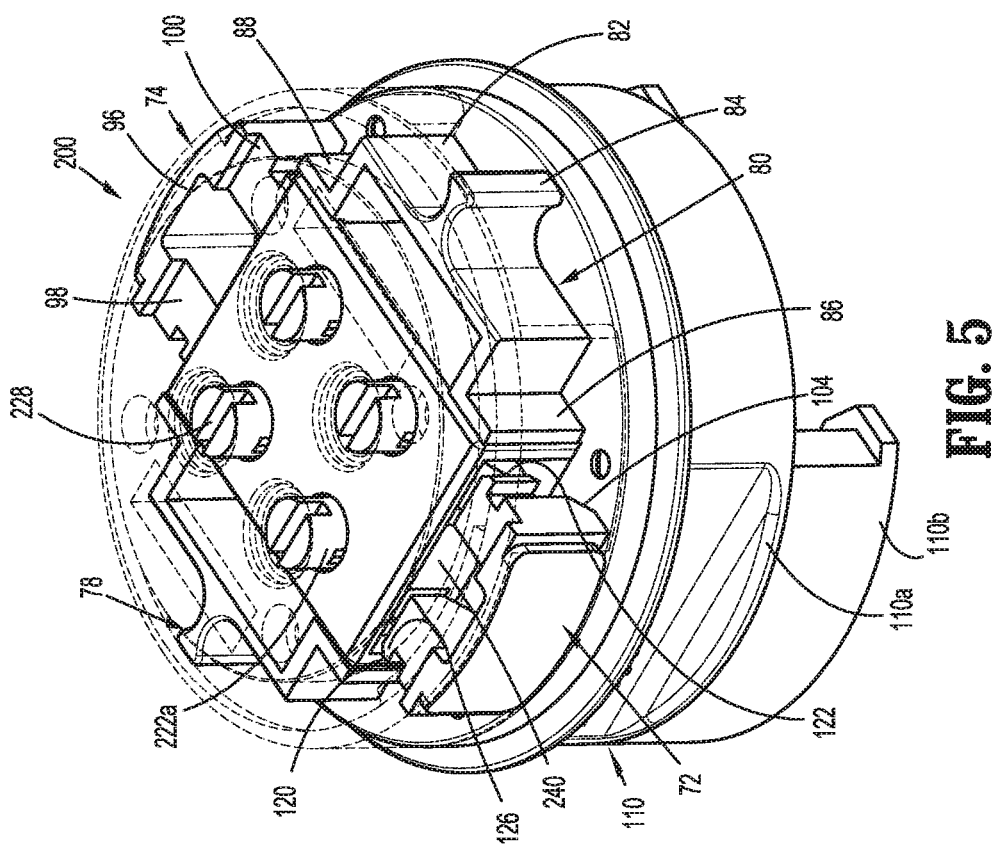
FIG. 5 is a perspective view illustrating buttons and pull tabs of the sterile interface module of FIG. 2.

The buttons 72, 74 of the release assembly 170 are spring biased outwardly by one or more springs 97 (FIG. 6A) toward a first position, such as, for example, an unactuated position (FIGS. 5, 6A). The buttons 72, 74 may be simultaneously depressed toward a second or actuated position (FIG. 9B, 11C) to activate an emergency release mechanism of the sterile interface module 200, as will be described. In some aspects, the release assembly 170 may only include one button.

Each of the buttons 72, 74 may have a generally U-shaped configuration and includes a body portion 96 and a pair of protuberances or protrusions 98, 100 extending inwardly from the body portion 96. A space 102 is defined between the protrusions 98, 100 of each of the buttons 72, 74 for receipt of a block portion 240 of a slider 226 of the sterile interface module 200. The protrusions 98, 100 of the buttons 72, 74 each have a camming surface 104, such as, for example, an oblique surface, configured to selectively engage with the slider 226 of the sterile interface module 200 to disconnect drive transfer assemblies 222 of the sterile interface module 200 from the drive members 76 of the instrument drive unit 70.

Turning now to FIGS. 4 and 7-9B, the main assembly 201 of the sterile interface module 200 generally includes a body member 210, a coupler assembly 212, a hub 214 (FIG. 4), and a slider 226. The body member 210 has an upper portion 210a and a lower portion 210b that are coupled together by one or more fasteners such as screws. The sterile interface module 200 includes pins 216 (e.g., pogo pins) that provide electrically conductive pathways through the sterile interface module 200 (e.g., to an end effector 60a of a surgical instrument 60 when surgical instrument 60 is coupled to the sterile interface module 200—see FIG. 1). The lower portion 210b of the body member 210 defines a ramped inner surface 218 configured to support a proximal end of the surgical instrument 60 thereon. The lower portion 210b of the body member 210 defines a recess 223 configured to receive an electromechanical surgical instrument, such as electromechanical surgical instrument 60, therein to removably secure the electromechanical surgical instrument 60 to the robotic surgical assembly 50. The upper portion 210a of the body member 210 defines drive transfer channels 220 that support drive transfer assemblies 222 therein.

Figure 4:
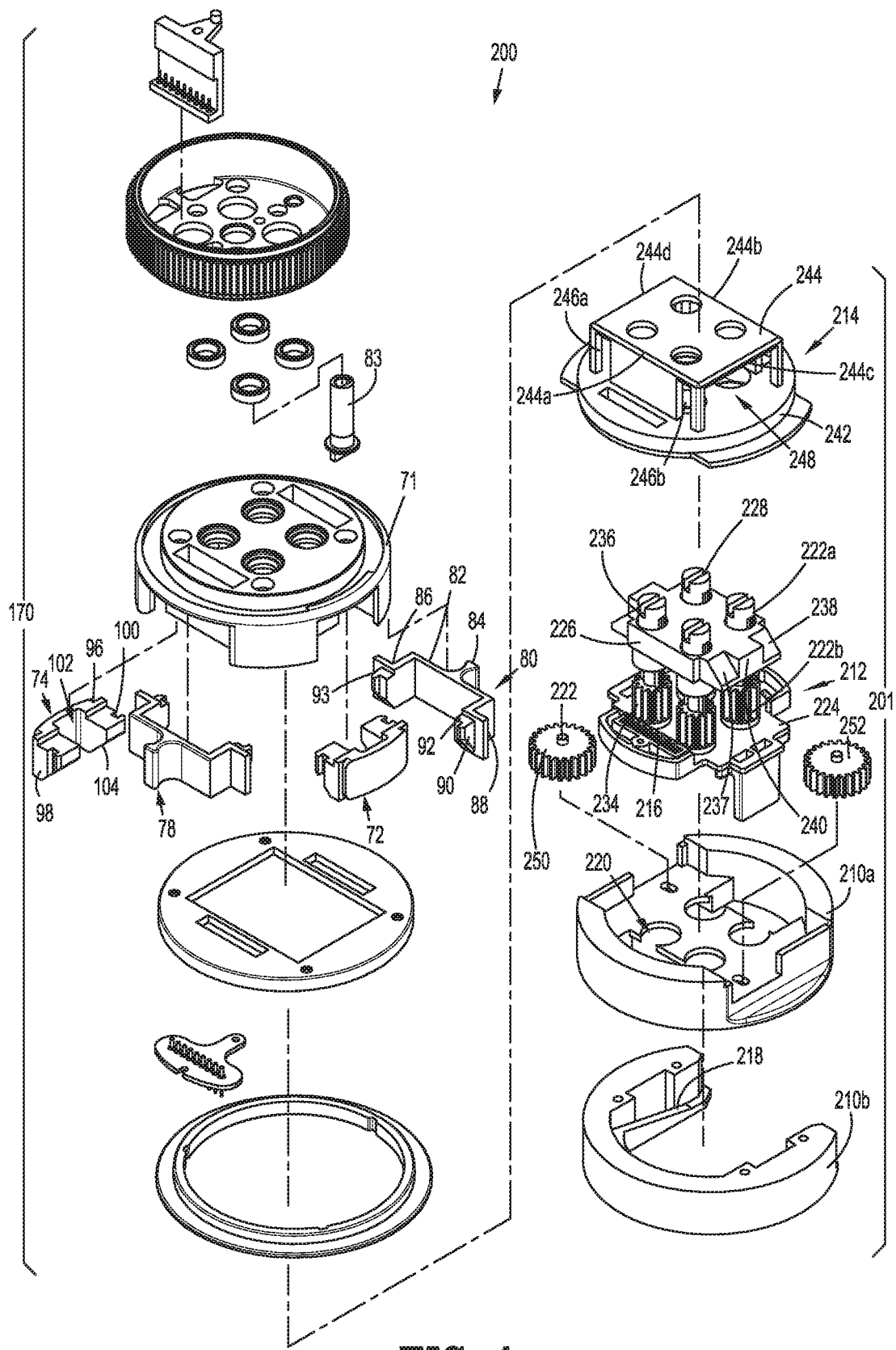
FIG. 4 is a perspective view, with parts separated, of the sterile interface module of FIG. 3.
Figure 9A:
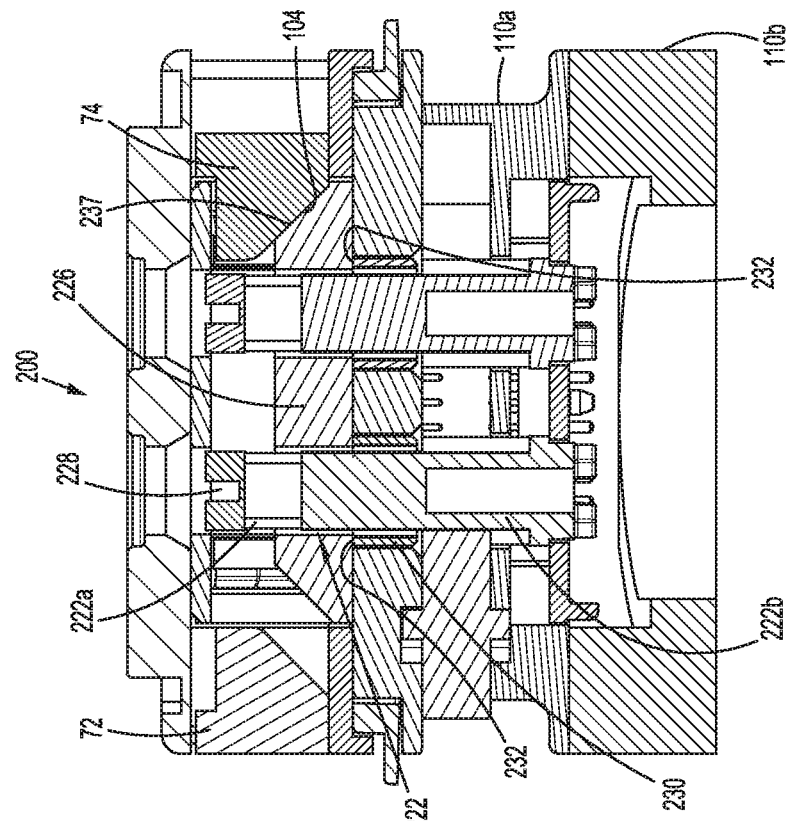
FIG. 9A is a longitudinal cross-sectional view illustrating the buttons disengaged from a slider of the sterile interface module.
Figure 9B:
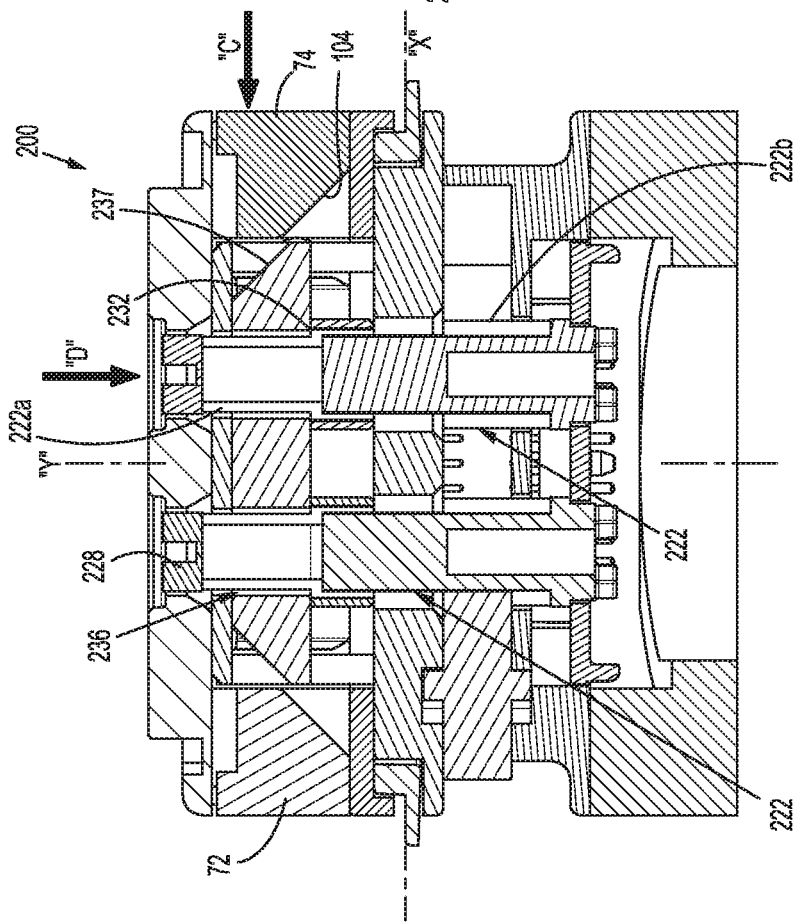
FIG. 9B is a longitudinal cross-sectional view illustrating one of the buttons engaged with the slider of the sterile interface module.

The coupler assembly 212 includes the drive transfer assemblies 222, a support plate 224 (FIG. 4) on which the drive transfer assemblies 222 are supported, and an actuator, such as, for example, the slider 226, supported on each of the drive transfer assemblies 222. As best shown in FIGS. 4, 9A, and 9B, each of the drive transfer assemblies 222 includes a proximal end portion, such as, for example, a proximal shaft 222a, and a distal end portion, such as, for example, a distal shaft 222b, coupled to the proximal shaft 222a. The proximal shaft 222a has a coupling end 228 (e.g., a slot) engagable with one of the respective drive shafts 76 (FIG. 3) of the instrument drive unit 70 on a proximal end of the proximal shaft 222a. The proximal shafts 222a have a sheath 230 disposed thereabout that defines a ledge 232 on which the slider 226 is supported.

The distal shafts 222b of the drive transfer assemblies 222 protrude distally through the respective openings 220 in the body member 210 and are configured to engage corresponding couplers (not shown) of the driven members of the electromechanical surgical instrument 60 (FIG. 1). The distal shaft 222b may be telescopically received in the proximal shaft 222a and resiliently biased in a distal direction. As such, the proximal shafts 222a float on the distal shafts 222b and are configured to move along and relative to the distal shafts 222b to selectively couple and decouple their coupling ends 228 from the respective drive shafts 76 of the instrument drive unit 70, as will be described. The distal shafts 222b each have a spur gear 234 fixed thereabout configured to selectively couple to a manual gear 250, 252 (e.g., a pinion gear) of the sterile interface module 200. In aspects, any suitable type of gear may be coupled to the distal shafts 222b.

The slider 226 of the coupler assembly 212 may have a generally flat, rectangular shape and defines a plurality of openings 236 therethrough. In aspects, the slider 226 may be block-shaped, planar, annular, and/or cylindrical. The openings 236 may be arranged in a squared configuration and have the drive couplers 228 of the proximal shafts 222a protruding proximally therefrom. The openings 236 in the slider 226 have a smaller inner diameter than the outer diameter of the sheath 230 of the proximal shafts 222a, such that the slider 226 is supported on the ledge 232 of the proximal shafts 222a. In this way, distal movement of the slider 226 results in distal movement of the proximal shaft 222a along and relative to the respective distal shafts 222b.

As best shown in FIGS. 4 and 8-9B, the slider 226 has opposite end portions 226a, 226b positioned adjacent respective buttons 72, 74 of the instrument drive unit 70 upon coupling the sterile interface module 200 to the instrument drive unit 70. The end portions 226a, 226 of the slider 226 each have a pair of camming surfaces 237, 238 and a block 240 disposed between the camming surfaces 237, 238. The camming surfaces 237, 238 are configured to be engaged by the camming surfaces 104 of the buttons 72, 74, such that movement of the buttons 72, 74 along a horizontal axis "X" (FIG. 9A) drives movement of the slider 226 distally along a vertical axis "Y" defined by the sterile interface module 200. In aspects, the slider 226 may be axially fixed to the proximal shafts 222a in any suitable manner, such as, for example, frictional engagement, adhesives, fasteners, or the like.

As best shown in FIG. 4, the hub 214 of the sterile interface module 200 may cover the components of the coupler assembly 212 and function as a connector for mechanically connecting the main assembly 201 of the sterile interface module 200 to the release assembly 170. The hub 214 has a base 242 fixed to the upper portion 210a of the body member 210 and a housing portion 244 attached to an upper surface of the base 242. The housing 244 of the hub 214 houses therein the slider 226 and the proximal shafts 222a of the drive transfer assemblies 222. The housing 244 of the hub 214 has a square-shaped configuration and includes a first pair of opposite sides 244a, 244b and a second pair of opposite sides 244c, 244d. The first pair of opposite sides 244a, 244b each defines a pair of apertures 246a, 246b dimensioned for receipt of the protrusions 86, 88 of the respective pull tabs 78, 80 for selectively axially fixing the sterile interface module 200 to the instrument drive unit 70. The second pair of opposite sides 244c, 244d each defines a passage 248 configured for receipt of the respective buttons 72, 74 during actuation of the buttons 72, 74.

Figure 8:
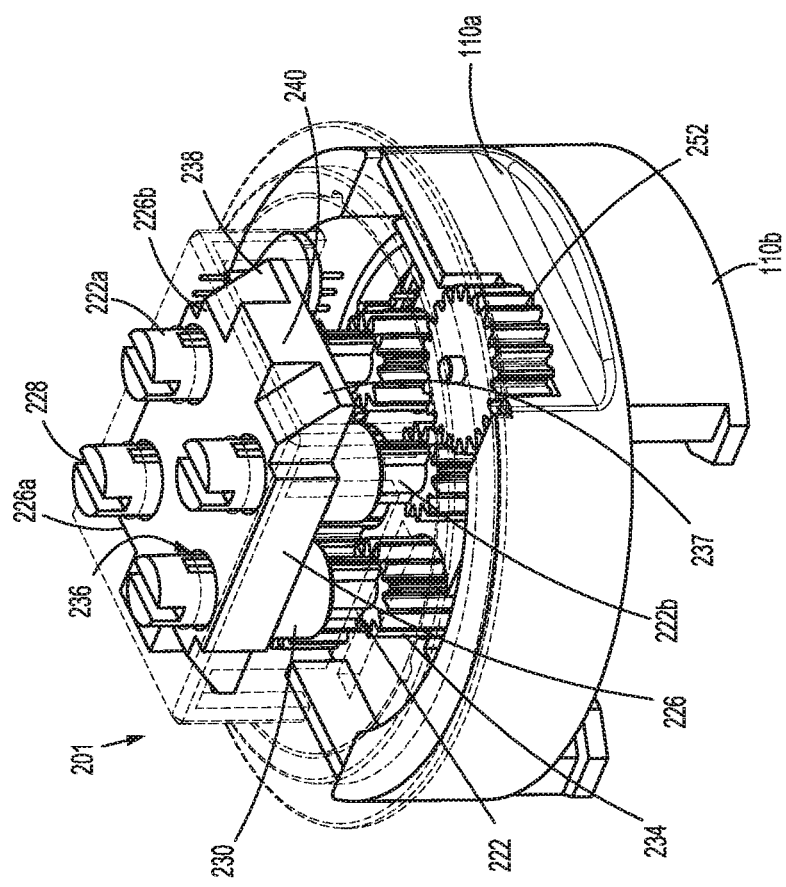
FIG. 8 is a perspective view, with parts shown in phantom, of the sterile interface module of FIG. 7.
Figure 7:
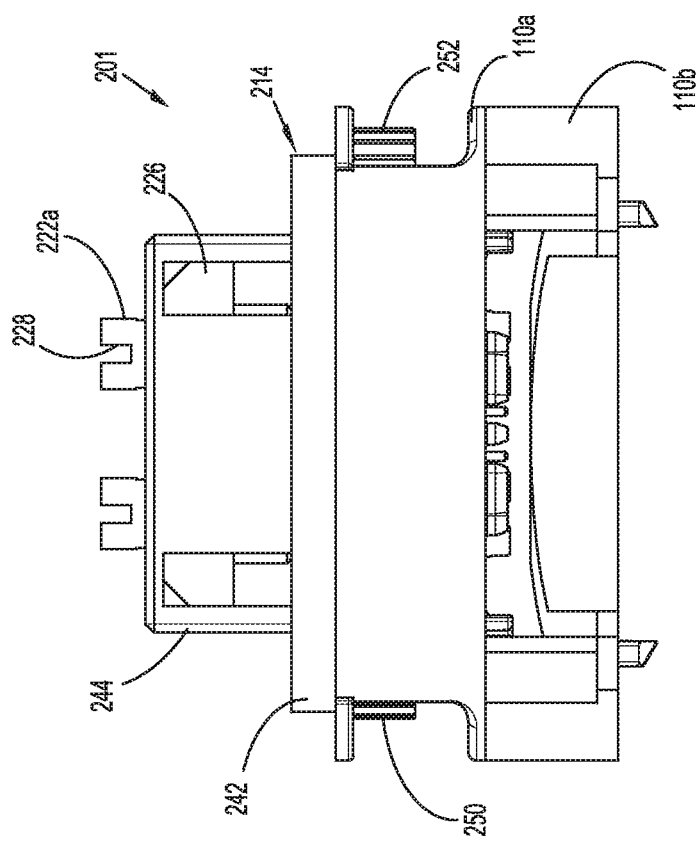
FIG. 7 is a front view of the sterile interface module of FIG. 2 with a release assembly thereof removed for clarity and illustration purposes.
Figure 10:
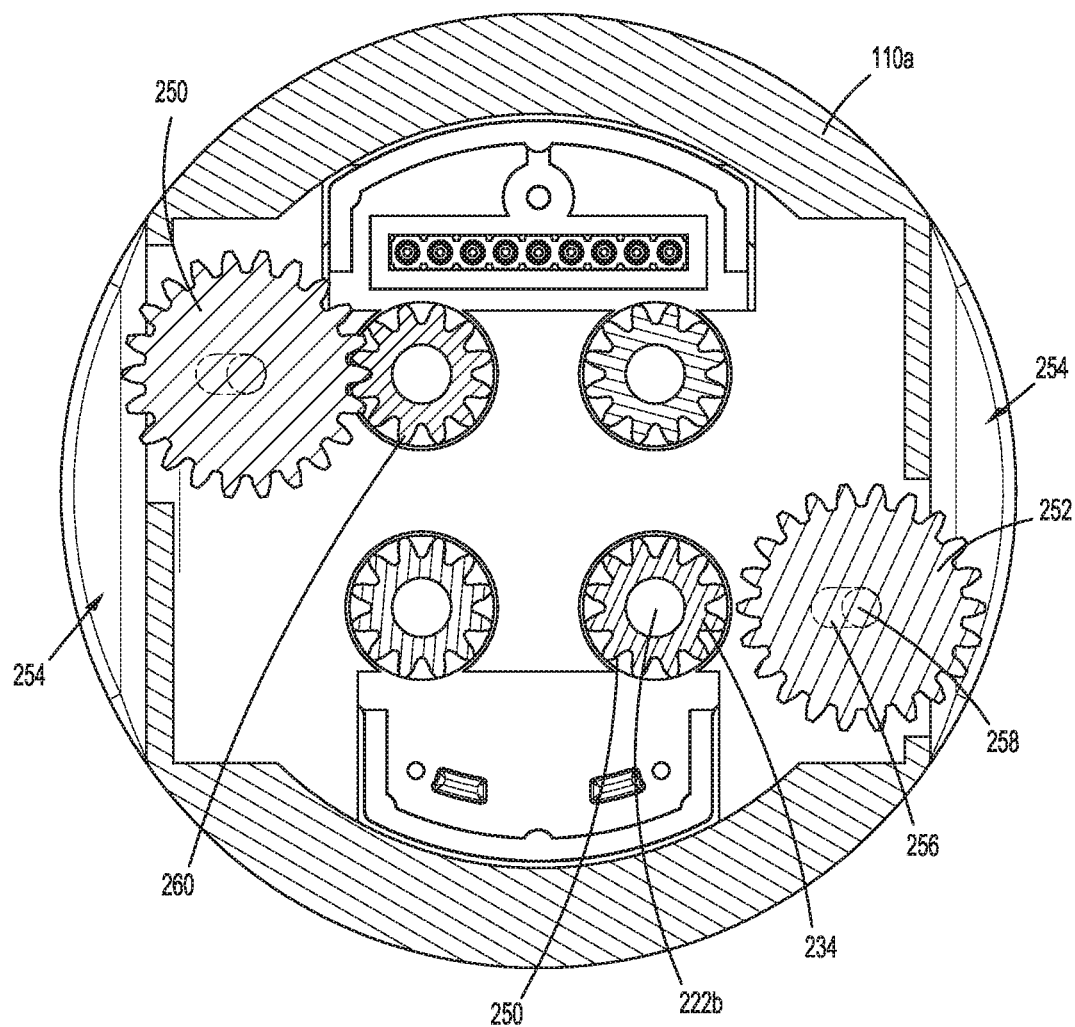
FIG. 10 is a transverse cross-sectional view illustrating a first gear of the sterile interface module engaged with a first drive transfer assembly of the sterile interface module and a second gear of the sterile interface module disengaged from a second drive transfer assembly of the sterile interface module.

With reference to FIGS. 4, 8, and 10, the sterile interface module 200 includes first and second manual gears 250, 252, such as, for example, pinion gears, rotationally and slidably supported on the upper portion 210a of the body member 210. In aspects, the sterile interface module 200 may include one or more manual gears. In further aspects, the sterile interface module 200 may include a manual gear associated with each of the drive transfer assemblies 222. The manual gears 250, 252 protrude outwardly through openings 254 in the upper portion 210a of the body member 210 to provide a clinician access to the manual gears 250, 252. The manual gears 250, 252 may have an elongate slot 256 defined therein through which a pin 258 is received. The elongate slot 256 allows the gears 250, 252 to slide between a disengaged position with associated gear teeth 260 of the distal shaft 222b, and an engaged position with the associated gear teeth 260 of the distal shaft 222b. In aspects, the gears 250, 252 may be resiliently biased toward the disengaged position by a biasing member (not shown) disposed in the slot 256. In other aspects, the manual gears 250, 252 may be permanently fixed in the engaged position.

An operation of the robotic surgical assembly 50 will now be described. With reference to FIGS. 6A and 6B, to couple the sterile interface module 200 to the instrument drive unit 70, the sterile interface module 200 is manipulated in a proximal direction to pass the hub 214 thereof into the collar 71 of the release assembly 170. The housing portion 244 engages the ramped surfaces 90, 93 of the pull tabs 78, 80, whereby the pull tabs 78, 80 are moved outwardly, in the direction indicated by arrow "A" in FIG. 6A, against the resilient bias of the spring members 83. With the first pair of sides 244a, 244b of the hub 214 of the sterile interface module 200 aligned with the corresponding pull tabs 78, 80, the pull tabs 78, 80 are biased by the spring members 83 inwardly, in the direction indicated by arrow "B" in FIG. 6B. The protrusions 86, 88 of the pull tabs 78, 80 are received in the corresponding apertures 246a, 246b in the hub 214 of the sterile interface module 200, such that the sterile interface module 200 is axially and rotationally fixed to the instrument drive unit 70. Upon coupling the sterile interface module 200 to the instrument drive unit 70, the drive couplers 228 of the drive transfer assemblies 222 of the sterile interface module 200 engage the corresponding drive members 76 (FIG. 3) of the instrument drive unit 70 to operably couple the sterile interface module 200 with the instrument drive unit 70.

With the robotic surgical assembly 50 of the robotic surgical system 1 secured to one of the surgical robotic arms 2, 3, of the robotic surgical system 1, and the electromechanical surgical instrument 60 of the robotic surgical system 1 secured to the sterile interface module 200 of the robotic surgical system 1, a clinician can perform a surgical procedure by robotically controlling the driven members of the electromechanical surgical instrument 60 with the motor assembly of the robotic surgical assembly 50 as desired. In particular, one or more of the motors of the motor assembly are actuated to rotate one or more of the drive members 76 of the of the motor assembly so that one or more of the drive transfer assemblies 222 of the sterile interface module 200 cooperate with one or more of the driven members of the electromechanical surgical instrument 60 to operate and/or manipulate the end effector 60a of the electromechanical surgical instrument 60 as desired (e.g., fire, articulate, rotate, etc.).

To decouple the sterile interface module 200 from the instrument drive unit 70, the release assembly 170 is actuated. In particular, the pull tabs 78, 80 are moved outwardly, in the direction indicated by arrow "A" in FIG. 6A, against the resilient bias of the spring members 83 to remove the protrusions 86, 88 of the pull tabs 78, 80 from the corresponding apertures 246a, 246b in the hub 214 of the main assembly 201. With the pull tabs 78, 80 of the release assembly 170 disengaged from the hub 214 of the main assembly 201, the main assembly 201 of the sterile interface module 200 may be disconnected from the instrument drive unit 70.

With reference to FIGS. 4, 9A, and 9B, in an emergency situation such as when there is an electrical power failure, and when the electromechanical surgical instrument 60 is at least partially positioned within a patient, a manual actuation of the surgical instrument 60 may be performed to manipulate the end effector 60a of the surgical instrument 60 despite the absence of power to the robotic surgical system 50. One or both of the buttons 72, 74 of the release assembly 170 are depressed to move the buttons 72, 74 inwardly, in the direction indicated by arrow "C" in FIG. 9A, from the starting position (FIG. 9A) toward an actuated position (FIG. 9B). The camming surfaces 104 of the buttons 72, 74 engage the camming surfaces 237, 238 of the slider 226, whereby the slider 2226 is driven distally, in the direction indicated by arrow "D" in FIG. 9A. Since the slider 226 is supported on the ledge 232 of the proximal shaft 222a of the drive transfer assemblies 222, the proximal shafts 222a move distally with the slider 226 and along the distal shafts 222b from an engaged position (FIG. 9A) to a disengaged position (FIG. 9B). In the disengaged position, the drive couplers 228 of the proximal shafts 222a are spaced distally from the drive shafts 76 (FIG. 3) of the instrument drive unit 70, and therefore not engaged therewith.

Figure 11C:
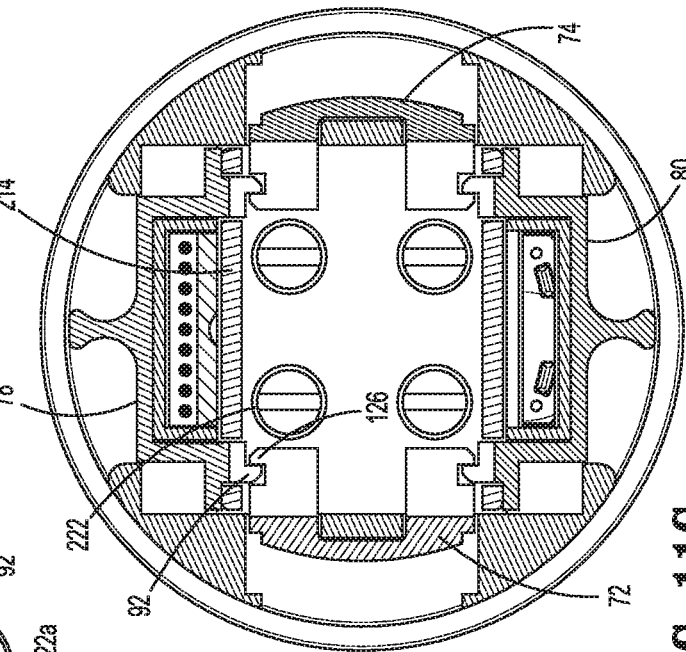
FIG. 11C is a transverse cross-sectional view illustrating the buttons lockingly engaged with the pull tabs.
Figure 11B:
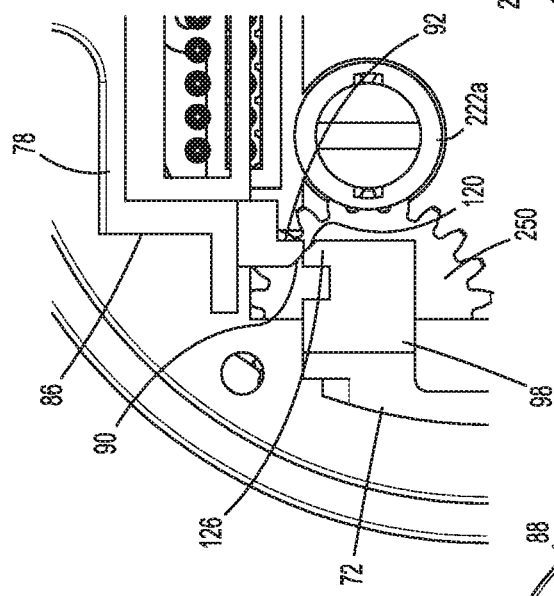
FIG. 11B is a transverse cross-sectional view, with parts removed, illustrating the buttons in an intermediate position relative to the pull tabs.
Figure 11A:
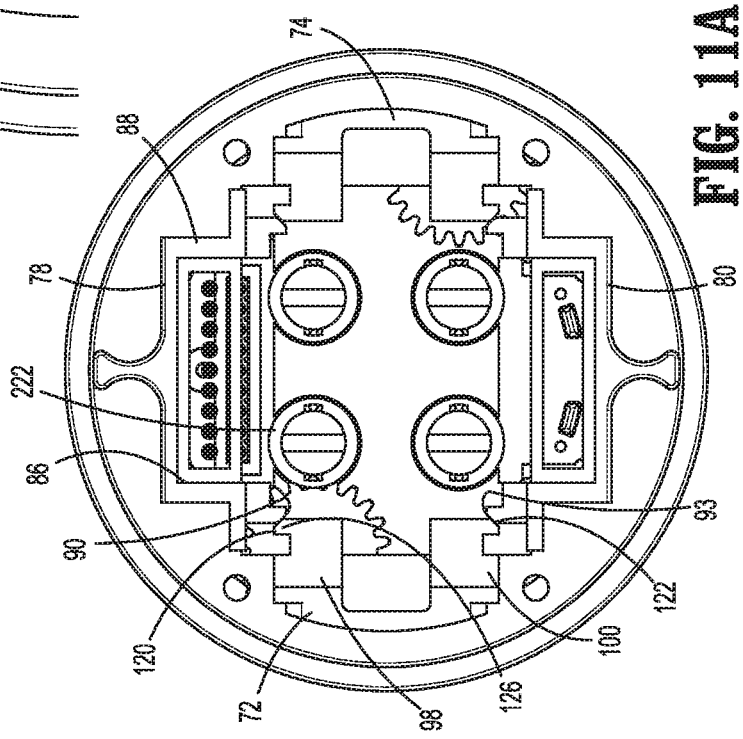
FIG. 11A is a transverse cross-sectional view, with parts removed, illustrating the buttons in an unlocked state with the pull tabs.

With reference to FIGS. 11A-11C, concurrently with the buttons 72, 74 engaging the slider 226, ramped surfaces 120, 122 defined on the respective protrusions 98, 100 of the buttons 72, 74 engage the ramped surfaces 90, 93 of the pull tabs 78, 80 (FIG. 11A) to drive the pull tabs 78, 80 outwardly, as shown in FIG. 11B. Continued application of an actuation force on the buttons 72, 74 moves the buttons 72, 74 to the actuated position, as shown in FIG. 11C. In the actuated position, the latches 126 of the buttons 72, 74 engage the latches 92 of the pull tabs 78, 80, whereby the pull tabs 78, 80 resist movement of the buttons 72, 74 out of the actuated position. In this way, a clinician does not have to maintain a force on the buttons 72, 74 to keep the buttons 72, 74 in the actuated position, in which the drive transfer assemblies 222 are disengaged from the drive members 76 of the instrument drive unit 70. With the drive transfer assemblies 222 maintained in the disengaged position by the connection between the pull tabs 78, 80 and the buttons 72, 74, a clinician may manually actuate the surgical instrument 60.

In particular, as shown in FIG. 10, one of the gears 250, 252 of the sterile interface module 200 may be pushed inwardly into engagement with gear teeth of 260 the distal shaft 222b. With one of the gears 250, 252 operably coupled with the distal shaft 222b, the gear 250 may be rotated, e.g., using a thumb of a clinician or any other suitable manner. Rotation of the gear 250 causes the associated distal shaft 222b to rotate, whereby the distal shaft 222b imparts forces (e.g., torque) through the respective components of the electromechanical surgical instrument 60 to manually manipulate the end effector 60a (FIG. 1) of the electromechanical surgical instrument 60 to position the end effector 60a in a desired orientation/position. For example, the end effector 60a of the electromechanical surgical instrument 60 can be manually manipulated to an open position to release tissue grasped by the end effector 60a so that the electromechanical surgical instrument 60 can be removed from a surgical site while limiting the risks of undesirable tissue damage that would otherwise be if such manual manipulation were not feasible when a power failure or other similar emergency situation arises.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the disclosure, and that such modifications and variations are also included within the scope of the disclosure. Accordingly, the subject matter of the disclosure is not limited by what has been particularly shown and described.

The invention claimed is:

1. An interface module for selective coupling between an electromechanical robotic surgical instrument and an instrument drive unit, the interface module comprising:
   a collar configured to be coupled to the instrument drive unit;
   a button supported by and movably coupled to the collar;
   a drive transfer assembly including:
      a distal end portion configured to couple to a driven member of the electromechanical robotic surgical instrument; and
      a proximal end portion movably coupled to the distal end portion and configured to selectively couple to a drive member of the instrument drive unit, wherein the proximal end portion of the drive transfer assembly is configured to move distally, in response to an actuation of the button, to disengage from the drive member of the instrument drive unit; and
   a gear selectively engageable with the distal end portion of the drive transfer assembly and manually rotatable to rotate the distal end portion of the drive transfer assembly when the drive transfer assembly is disengaged from the drive member of the instrument drive unit.

2. The interface module according to claim 1, wherein the button is movable along a first axis to move the proximal end portion of the drive transfer assembly along a second axis, perpendicular to the first axis, between an engaged position, in which the drive transfer assembly is engaged with the drive member of the instrument drive unit and a disengaged position, in which the drive transfer assembly is disengaged from the drive member of the instrument drive unit.

3. The interface module according to claim 1, wherein the interface module further includes a slider supported on the proximal end portion of the drive transfer assembly and configured to engage the button, the proximal end portion of the drive transfer assembly being configured to move axially with the slider.

4. The interface module according to claim 3, wherein the slider has a camming surface and the button has a camming surface configured to engage the camming surface of the slider to distally move the slider, and in turn, the proximal end portion of the drive transfer assembly.

5. The interface module according to claim 3, further comprising a hub, wherein the slider and the proximal end portion of the drive transfer assembly are housed within the hub.

6. The interface module according to claim 1, further comprising a pull tab movably coupled to the collar and configured to releasably couple the interface module to the instrument drive unit.

7. The interface module according to claim 6, further comprising a hub defining an aperture therein, wherein the pull tab includes a protrusion configured to be received in the aperture of the hub to axially fix the hub to the collar.

8. The interface module according to claim 7, wherein the pull tab is manually movable between a first position, in which the protrusion of the pull tab is engaged with the aperture of the hub whereby the hub is lockingly engaged with the collar, and a second position, in which the protrusion of the pull tab is disengaged from the aperture of the hub whereby the hub is unlocked from the collar.

9. The interface module according to claim 6, wherein the pull tab is configured to lockingly engage the button when the button is actuated, such that the pull tab maintains the button in an actuated position to maintain the proximal end portion of the drive transfer assembly disengaged from the drive member of the instrument drive unit.

10. The interface module according to claim 9, wherein the pull tab has a latch and the button has a latch that engages the latch of the pull tab when the button is moved to the actuated position, the latch of the pull tab being configured to resist movement of the button out of the actuated position.

11. The interface module according to claim 10, wherein the pull tab is configured to move between an inward position and an outward position, the latch of the pull tab being configured to disengage the latch of the button in response to movement of the pull tab toward the outward position.

12. The interface module according to claim 1, wherein the distal end portion of the drive transfer assembly has gear teeth extending thereabout.

13. The interface module according to claim 12, wherein the gear is slidable relative to the drive transfer assembly between a first position, in which the gear is disengaged from the gear teeth of the distal end portion of the drive transfer assembly, and a second position, in which the gear is engaged with the gear teeth of the distal end portion of the drive transfer assembly.

14. A sterile interface module for selective coupling between an instrument drive unit and a surgical instrument, the sterile interface module comprising:
a body member configured to selectively couple to the surgical instrument;
a hub supported on the body member;
a plurality of drive transfer assemblies supported on the body member, each of the plurality of drive transfer assemblies being rotatable about a respective axis thereof; each of the plurality of drive transfer assemblies including:
a proximal end portion configured to selectively couple to a drive member of the instrument drive unit; and
a distal end portion configured to selectively couple to a driven member of the surgical instrument, the proximal end portion being axially movable relative to the distal end portion; and
a slider supported on the proximal end portion of each of the plurality of drive transfer assemblies and slidable in a direction parallel to the axis of rotation of each drive transfer assembly, wherein the proximal end portions for all of the drive transfer assemblies move distally relative to the respective distal end portion of the plurality of drive transfer assemblies to disengage from the respective drive member of the instrument drive unit in response to distal movement of the slider.

15. The sterile interface module according to claim 14, wherein the slider defines a plurality of openings therethrough, the proximal end portion of each of the plurality of drive transfer assemblies extending through the respective opening.

16. The sterile interface module according to claim 14, wherein the slider includes an end portion having a camming surface.

17. The sterile interface module according to claim 14, further comprising a gear rotationally supported on the body member and configured to selectively engage the distal end portion of at least one of the plurality of drive transfer assemblies.

18. The sterile interface module according to claim 17, wherein the gear is slidable relative to the body member between a first position, in which the gear is disengaged from the distal end portion of the at least one of the plurality of drive transfer assemblies, and a second position, in which the gear is engaged to the distal end portion of the at least one of the plurality of drive transfer assemblies.

19. The sterile interface module according to claim 14, wherein the hub has a squared configuration and includes a first side defining a pair of apertures for receipt of a pair of protrusions of a pull tab, and a second side adjoining the first side and defining a passage for receipt of a button.

20. A sterile interface module for selective coupling between an electromechanical robotic surgical instrument and an instrument drive unit, the sterile interface module comprising:
a pull tab having a protrusion; and
a drive transfer assembly for coupling a driven member of the electromechanical robotic surgical instrument and a drive member of the instrument drive unit; and
a hub having at least a portion of the drive transfer assembly disposed therein, the hub defining an aperture, the protrusion of the pull tab being disposed within the aperture of the hub, wherein the pull tab is configured to move between a first position, in which the protrusion of the pull tab is engaged with the aperture of the hub to axially fix the sterile interface module to the instrument drive unit, and a second position, in which the protrusion of the pull tab is disengaged from the aperture of the hub.

21. The sterile interface module according to claim 20, wherein the pull tab is resiliently biased toward the first position.

22. The sterile interface module according to claim 20, further comprising a button operably coupled to the drive transfer assembly and configured to disconnect the drive transfer assembly from the drive member of the instrument drive unit when the button is in an actuated position.

23. The sterile interface module according to claim 22, wherein the pull tab is configured to lockingly engage the button, such that the pull tab maintains the button in the actuated position to maintain the drive transfer assembly disconnected from the drive member of the instrument drive unit.

24. The sterile interface module according to claim 23, wherein the pull tab has a latch and the button has a latch that engages the latch of the pull tab when the button is moved to the actuated position, the latch of the pull tab being configured to resist movement of the button out of the actuated position.

25. The sterile interface module according to claim 24, wherein the pull tab is configured to move between an inward position and an outward position, the latch of the pull tab being configured to disengage the latch of the button in response to movement of the pull tab toward the outward position.

* * * * *